US012694980B2

(12) United States Patent
Ravishankar et al.

(10) Patent No.: US 12,694,980 B2
(45) Date of Patent: Jul. 28, 2026

(54) METHODS AND SYSTEM FOR CARDIAC ARRHYTHMIA PREDICTION USING TRANSFORMER-BASED NEURAL NETWORKS

(71) Applicant: GE Precision Healthcare LLC, Wauwatosa, WI (US)

(72) Inventors: Hariharan Ravishankar, Bengaluru (IN); Rohan Keshav Patil, Bengaluru (IN); Abhijit Patil, Bengaluru (IN); Heikki Paavo Aukusti Väänänen, Uusimaa (FI)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 1163 days.

(21) Appl. No.: 17/648,920

(22) Filed: Jan. 25, 2022

(65) Prior Publication Data
US 2023/0238134 A1 Jul. 27, 2023

(51) Int. Cl.
| | |
|---|---|
| *G06N 20/00* | (2019.01) |
| *A61B 5/361* | (2021.01) |
| *A61B 5/363* | (2021.01) |
| *G06N 3/045* | (2023.01) |
| *G16H 15/00* | (2018.01) |
(Continued)

(52) U.S. Cl.
CPC ............. *G16H 50/20* (2018.01); *A61B 5/361* (2021.01); *A61B 5/363* (2021.01); *G06N 3/045* (2023.01); *G16H 15/00* (2018.01); *G16H 40/63* (2018.01); *G16H 50/30* (2018.01); *G06N 20/00* (2019.01)

(58) Field of Classification Search
None
See application file for complete search history.

(56) References Cited

U.S. PATENT DOCUMENTS

| | | | |
|---|---|---|---|
| 2018/0206797 A1* | 7/2018 | Samiee ................ | A61B 5/7275 |
| 2020/0155025 A1* | 5/2020 | Smith .................. | A61B 5/7264 |
(Continued)

FOREIGN PATENT DOCUMENTS

WO     WO-2021081418 A1 *   4/2021   ............. G10L 25/63

OTHER PUBLICATIONS

Cho Jungrae et al: "Prediction to Atrial Fibrillation Using Deep Convolutional Neural Networks", Sep. 13, 2018 (Sep. 13, 2018), SAT 2015 18th International Conference, Austin, TX, USA, Sep. 24-27, 2015; [Lecture Notes in Computer Science; Lect.Notes Computer], Springer, Berlin, Heidelberg, pp. 164-171, XP047485346, ISBN: 978-3-540-7 4549-5 [retrieved on Sep. 13, 2018].
(Continued)

*Primary Examiner* — Xuyang Xia
(74) *Attorney, Agent, or Firm* — McCoy Russell LLP

(57) ABSTRACT

Methods and systems are provided for predicting cardiac arrhythmias based on multi-modal patient monitoring data via deep learning. In an example, a method may include predicting an imminent onset of a cardiac arrhythmia in a patient, before the cardiac arrhythmia occurs, by analyzing patient monitoring data via a multi-arm deep learning model, outputting an arrhythmia event in response to the prediction, and outputting a report indicating features of the patient monitoring data contributing to the prediction. In this way, the multi-arm deep learning model may predict cardiac arrhythmias before their onset.

14 Claims, 7 Drawing Sheets

(51) Int. Cl.

| | |
|---|---|
| *G16H 40/63* | (2018.01) |
| *G16H 50/20* | (2018.01) |
| *G16H 50/30* | (2018.01) |

(56) References Cited

U.S. PATENT DOCUMENTS

| | | | |
|---|---|---|---|
| 2022/0039729 A1* | 2/2022 | Fontanarava | A61B 5/7264 |
| 2022/0198254 A1* | 6/2022 | Dalli | G06N 3/094 |
| 2022/0225901 A1* | 7/2022 | Chapman | A61B 5/1495 |

OTHER PUBLICATIONS

EP application 23150966.2 filed Jan. 10, 2023—extended Search Report issued Jun. 15, 2023; 31 pages.

Gilon Cedric et al: "Forecast of paroxysmal atrial fibrillation using a deep neural network", 2020 International Joint Conference on Neural Networks (IJCNN), IEEE, Jul. 19, 2020 (Jul. 19, 2020), pp. 1-7, XP033831552, DOI: 10.1109/IJCNN48605.2020.9207227 [retrieved on Sep. 25, 2020].

"Ventricular fibrillation," Wikipedia Website, Available Online at https://en.wikipedia.org/wiki/Ventricular_fibrillation, Available as Early as Feb. 16, 2003, 9 pages.

"Atrial fibrillation," Wikipedia Website, Available Online at https://en.wikipedia.org/wiki/Atrial_fibrillation, Available as Early as Sep. 27, 2003, 41 pages.

Fujita, H. et al., "Sudden cardiac death (SCD) prediction based on nonlinear heart rate variability features and SCD Index," Applied Soft Computing, vol. 43, Jun. 2016, 31 pages.

Figuera, C. et al., "Machine Learning Techniques for the Detection of Shockable Rhythms in Automated External Defibrillators," PLOS ONE, vol. 11, No. 7, Jul. 21, 2016, 17 pages.

Shao, M. et al., "Detection of atrial fibrillation from ECG recordings using decision tree ensemble with multi-level features," Physiological Measurement, vol. 39, No. 9, Sep. 27, 2018, 17 pages.

Taye, G. et al., "Machine Learning Approach to Predict Ventricular Fibrillation Based on QRS Complex Shape," Frontiers in Physiology, vol. 10, Sep. 20, 2019, 10 pages.

Yan, G. et al., "Fusing Transformer Model with Temporal Features for ECG Heartbeat Classification," Proceedings of the 2019 IEEE International Conference on Bioinformatics and Biomedicine (BIBM), Nov. 18, 2019, San Diego, California, 12 pages.

Taye, G. et al., "Application of a convolutional neural network for predicting the occurrence of ventricular tachyarrhythmia using heart rate variability features," Scientific Reports, vol. 10, No. 6769, Apr. 21, 2020, 7 pages.

Mandala, S. et al., "ECG-based prediction algorithm for imminent malignant ventricular arrhythmias using decision tree, " PLOS ONE, vol. 15, No. 5, May 14, 2020, 20 pages.

Tseng, L. et al., "Predicting Ventricular Fibrillation Through Deep Learning," IEEE Access, vol. 8, Dec. 7, 2020, 11 pages.

Rahul, J. et al., "An improved cardiac arrhythmia classification using an RR interval-based approach," Biocybernetics and Biomedical Engineering, vol. 41, No. 2, Apr. 2021, 11 pages.

Che, C. et al., "Constrained transformer network for ECG signal processing and arrhythmia classification," BMC Medical Informatics and Decision Making, vol. 21, No. 184, Jun. 9, 2021, 13 pages.

"Arrhythmia," National Heart, Lung, and Blood Institute Website, Available Online at https://www.nhlbi.nih.gov/health-topics/arrhythmia, Retrieved on Jan. 13, 2021, 27 pages.

* cited by examiner

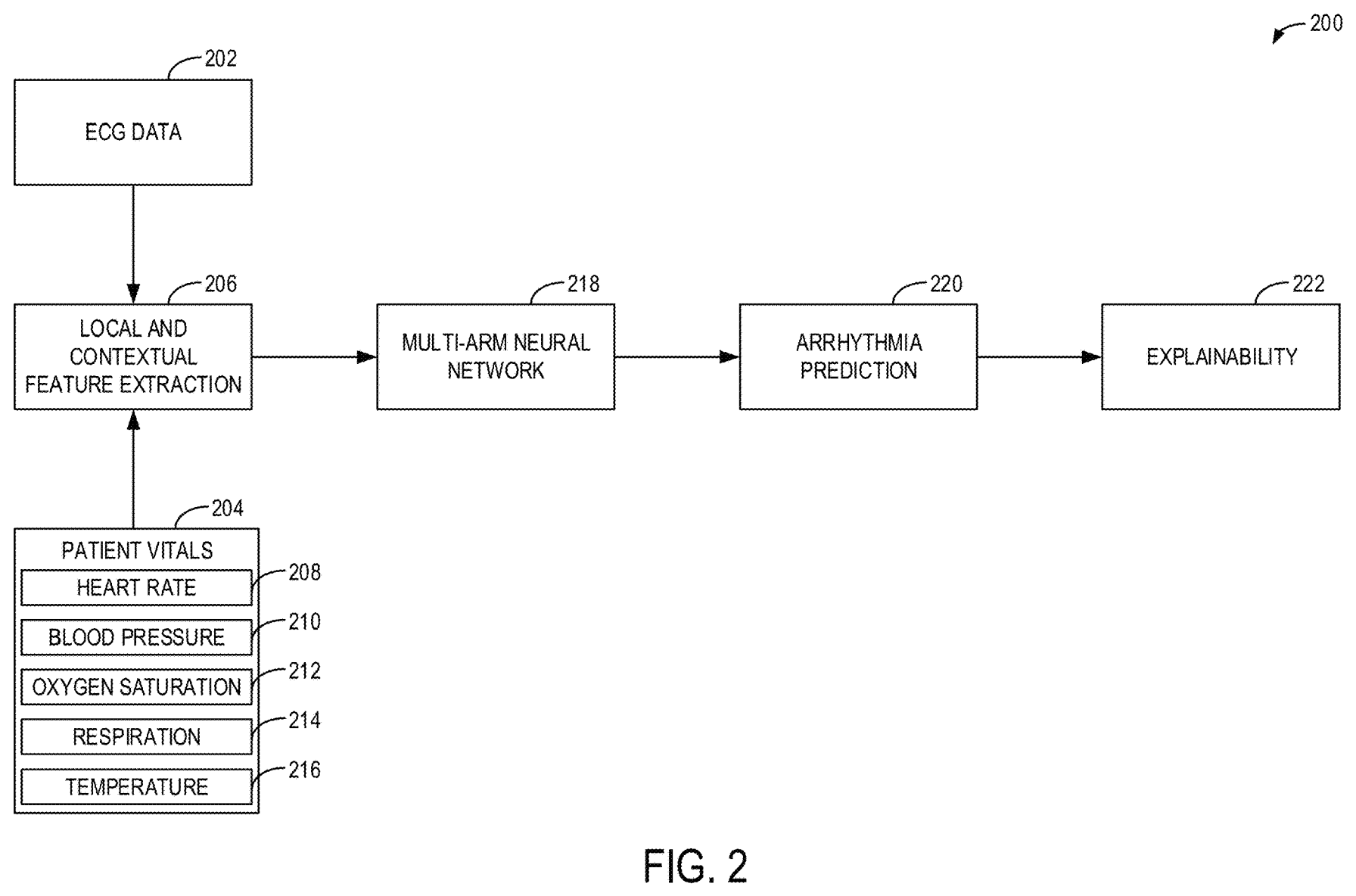

200

ECG DATA
202

LOCAL AND
CONTEXTUAL
FEATURE EXTRACTION
206

PATIENT VITALS
204

HEART RATE
208

BLOOD PRESSURE
210

OXYGEN SATURATION
212

RESPIRATION
214

TEMPERATURE
216

MULTI-ARM NEURAL
NETWORK
218

ARRHYTHMIA
PREDICTION
220

EXPLAINABILITY
222

FIG. 2

METHODS AND SYSTEM FOR CARDIAC ARRHYTHMIA PREDICTION USING TRANSFORMER-BASED NEURAL NETWORKS

FIELD

Embodiments of the subject matter disclosed herein relate to predicting cardiac arrhythmia based on multi-modal data using deep neural networks.

BACKGROUND

Cardiac arrhythmias include irregular or abnormal heart rhythms caused by improper beating of the heart and lead to poor blood flow from the heart to the remainder of the body. Some arrhythmias, such as ventricular tachycardia (VT) and ventricular fibrillation (VF), may result in cardiac arrest and stopped pulse. Similarly, atrial fibrillation (AF) may result in heart failure, dementia, stroke, and other undesired health consequences. While existing algorithms may detect these arrhythmias when they occur, they do no predict the onset of these events before they occur. As a result, there may be a delay between arrhythmia detection and healthcare providers being able to respond with appropriate interventions.

SUMMARY

In one aspect, a method includes predicting an imminent onset of a cardiac arrhythmia in a patient, before the cardiac arrhythmia occurs, by analyzing patient monitoring data via a multi-arm deep learning model, outputting an arrhythmia event in response to the prediction, and outputting a report indicating features of the patient monitoring data contributing to the prediction.

The above advantages, other advantages, and features of the present description will be readily apparent from the following detailed description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 2 shows a high-level block diagram of a workflow for cardiac arrhythmia prediction.

DETAILED DESCRIPTION

Embodiments of the present disclosure will now be described, by way of example, with reference to the FIGS. 1-7, which relate to various embodiments for predicting cardiac arrhythmias based on patient monitoring data using deep neural networks. The description further discloses systems and methods for training said deep neural networks and understanding the factors behind the arrhythmia predictions. In this way, the deep neural networks may support clinical decision making.

Some cardiac arrhythmias, such as ventricular tachycardia (VT) and ventricular fibrillation (VF), are shockable (e.g., with a defibrillator) but may have different speeds of progression. For example, the onset of VT or VF may be sudden, occurring over a few seconds to minutes, or deteriorating (e.g., progressing over minutes to hours). While existing algorithms may detect such cardiac arrhythmias as they occur in a patient, they may not predict the onset of these events prior to their occurrence. As a result, clinicians may not be prepared to intervene on the patient. Because positive patient outcomes are reduced as a function of time during some cardiac arrhythmias, delays in interventions and treatment may lead to poorer patient prognoses. However, it may be challenging to construct an accurate prediction model that is capable of analyzing short-term temporal dynamics (e.g., rhythm changes) as well as long-term dynamics (e.g., heart rate variability).

The present disclosure at least partially addressed the above described issues by providing an architecture for multi-scale temporal analysis using neural networks that enable more accurate cardiac arrhythmia prediction. A benefit that may be achieved through practice of the present disclosure is that cardiac arrhythmias occurring over different timescales may be proactively treated. For example, predicting the onset of cardiac arrhythmias in advance may result in early interventions and treatments that may increase positive patient outcomes.

Figure 1:
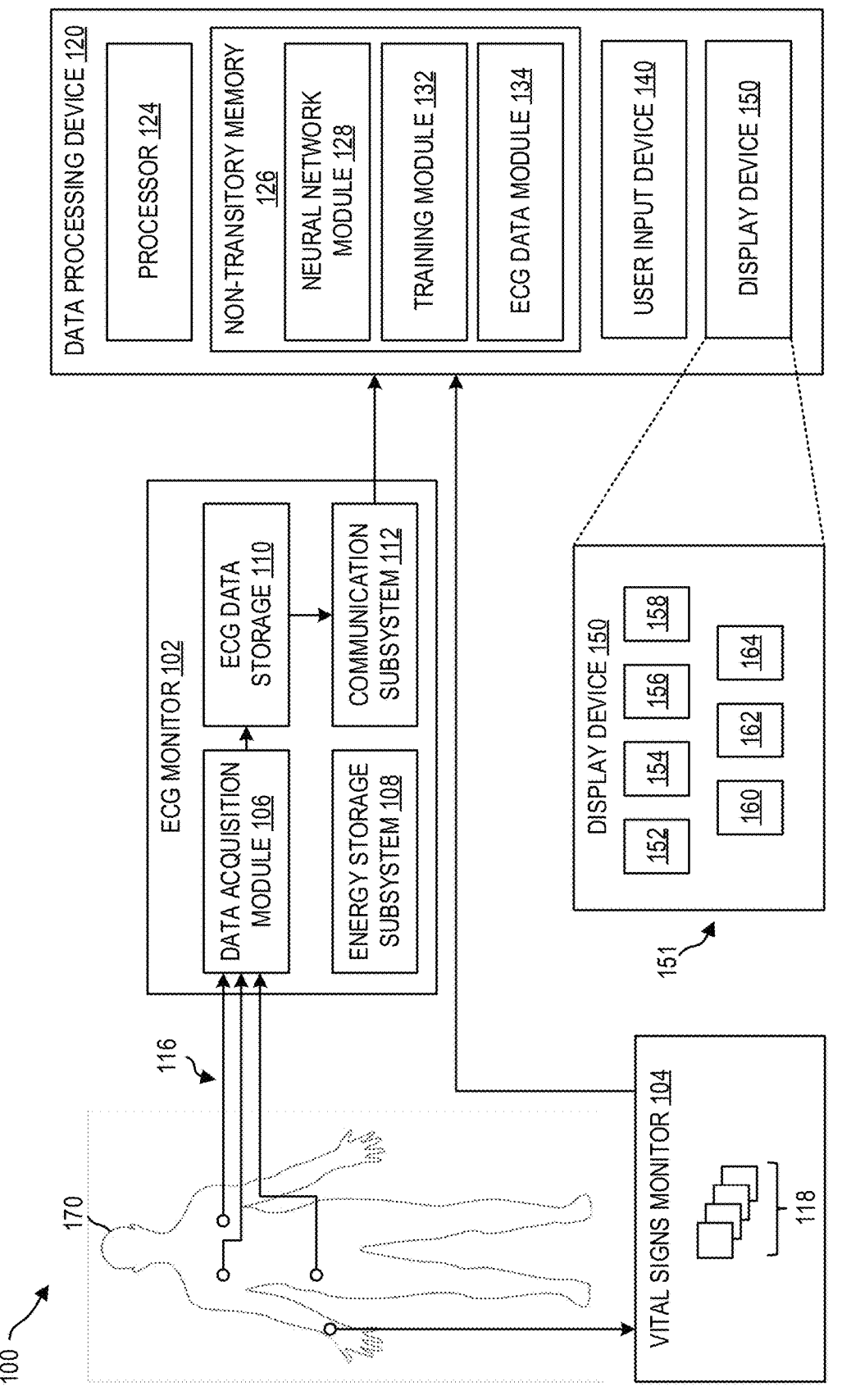
FIG. 1 shows a block diagram of a patient monitoring system, including an electrocardiogram (ECG) monitor.
Figure 6:
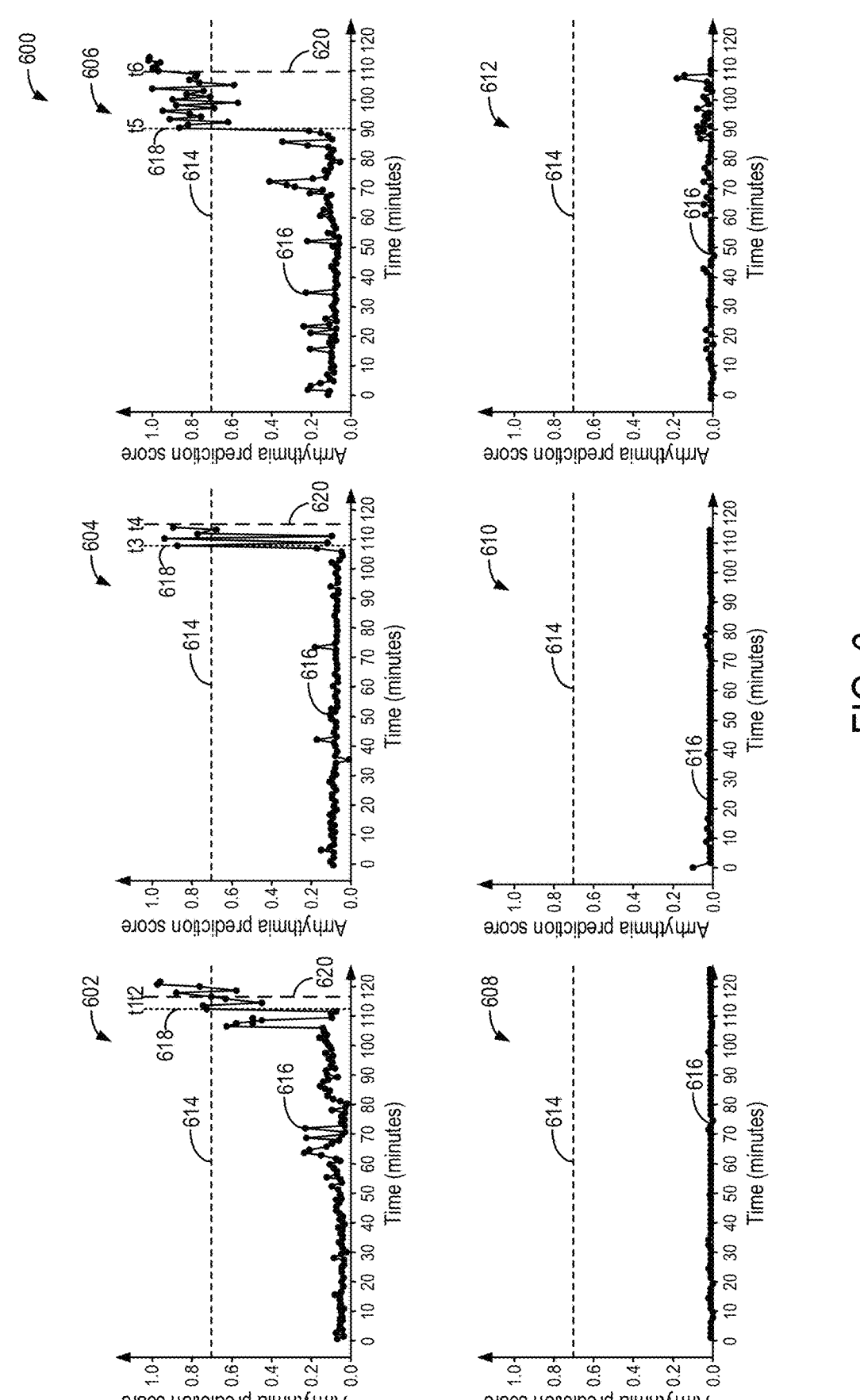
FIG. 6 shows a set of graphs illustrating ventricular fibrillation prediction from ECGs.
Figure 7:
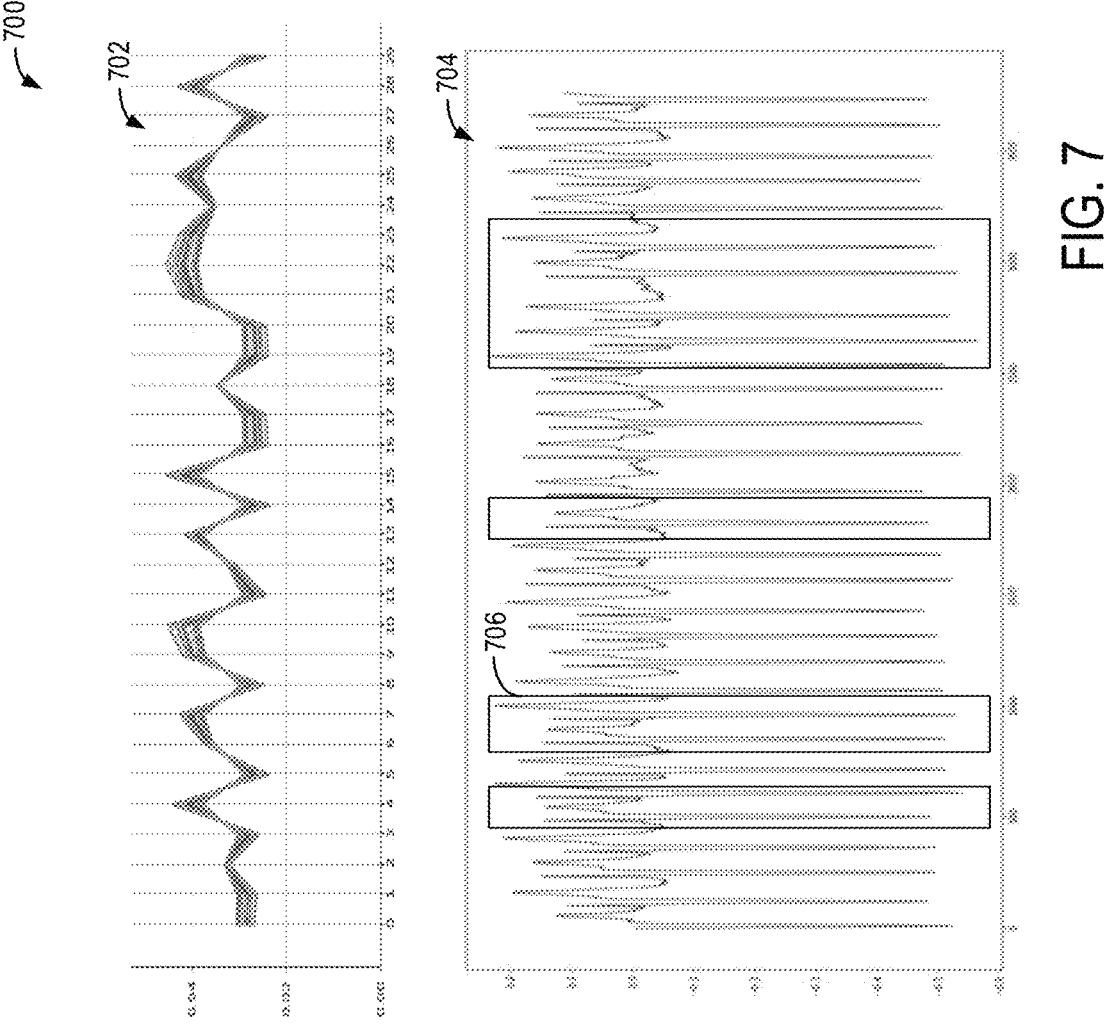
FIG. 7 shows a set of graphs illustrating prediction explainability.
Figure 7:
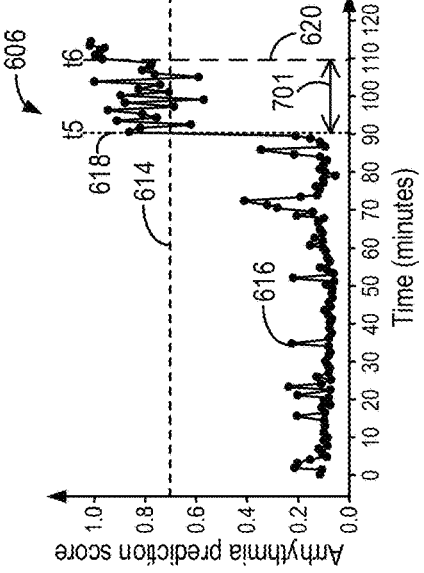

FIG. 1 shows a patient monitoring system that may be used to acquire patient monitoring data, which may include electrocardiogram (ECG) data or multi-modal data including the ECG data and data from a plurality of sensors acquiring vital signs. The patient monitoring data may undergo feature extraction and modeling on different timescales to predict cardiac arrhythmias, such as according to the workflow shown in FIG. 2. For example, a tri-net neural network a may be used to predict the cardiac arrhythmias that includes a three-arm network architecture for modeling data at different timescales, such as diagrammed in FIG. 3. The tri-net neural architecture may be trained via the method of FIG. 4 and utilized to predict cardiac arrhythmias via the method of FIG. 5. Further, FIG. 6 shows a set of graphs demonstrating ventricular fibrillation prediction, and FIG. 7 shows a set of graphs illustrating prediction explainability. The prediction explainability may be used by healthcare providers to assess the features from the patient monitoring data that resulted in the cardiac arrhythmia prediction, thus providing input for clinical decision making. In this way, healthcare providers may be alerted to the development of cardiac arrhythmias prior to their onset, enabling the healthcare providers to prepare an appropriate intervention. As a result, an amount time until the cardiac arrhythmia is treated may be decreased, which may increase positive patient outcomes.

Turning now to the figures, FIG. 1 shows an embodiment of a patient monitoring system 100. The patient monitoring system 100 comprises an ECG monitor 102, a vital sign monitor 104, and a data processing device 120 communicably coupled thereto. The ECG monitor 102 is configured to measure and store a recording of the electrical activity of the heart of a patient 170 and comprises a plurality of electrodes 116. The ECG data recorded by the ECG monitor 102 comprises time series data, wherein an electrical potential (voltage) between two or more electrodes 116 in electrical contact with the skin of the patient 170 is recorded as a function of time. Although FIG. 1 includes the ECG monitor 102, it may be appreciated that other devices that record heart activity through time may be used, such as an inertial sensor that records periodic movement, for example.

The ECG data acquired by the ECG monitor 102 may be transferred to the data processing device 120 for further processing before being evaluated by a healthcare professional, such as a cardiologist. The healthcare professional may evaluate the ECG data acquired by the ECG monitor 102 for signs of an arrhythmia or another cardiac disorder. In one embodiment, to facilitate evaluation of the ECG data acquired by the ECG monitor 102, the data processing device 120 may employ a three-arm trained neural network, referred to herein as a "tri-net," to predict cardiac arrhythmias before they occur based on the ECG data alone or in combination with data from the vital sign monitor 104, described in more detail below with reference to FIGS. 2-5. The tri-net may output an arrhythmia event as well as an explainability report of features leading to the arrhythmia prediction that may be presented to the cardiologist.

In the embodiment shown in FIG. 1, the plurality of electrodes 116 include a right arm electrode, a left arm electrode, and leg electrode, which are attached to the patient 170 via adhesive pads and/or electrically conductive gel. Thus, in the present example, the plurality of electrodes 116 are configured to measure a three lead ECG, wherein the electrical potential is measured along three distinct axes passing through the heart of the patient 170. However, it may be appreciated that the ECG monitor 102 may comprise more or fewer than three electrodes. For example, the ECG monitor 102 may obtain single-lead ECG data. Similarly, the placement of the electrodes 116 on the patient 170 may differ from that described above without departing from the scope of this disclosure.

The plurality of electrodes 116 may be electrically coupled to a data acquisition module 106 of the ECG monitor 102. The data acquisition module 106 is configured to measure electrical potential differences between two or more of the plurality of electrodes 116 as a function of time and record the measurement in an ECG data storage 110. In some embodiments, the data acquisition module 106 may be configured to receive analog electrical signals from the plurality of electrodes 116, amplify and/or filter the analog signals, and convert the analog signals to digital signals before storing the digital signals as a function of time in the ECG data storage 110. In another embodiment, the data acquisition module 106 may convert the analog electrical signals from the plurality of electrodes 116 to a digital signal and may amplify and/or filter the digital signal before storing the digital signal as a function of time in the ECG data storage 110. In some embodiments, the data acquisition module 106 may be configured to differential amplify signals from each lead, thereby adjusting for differences in signal intensity.

The data acquisition module 106 is communicably coupled with the ECG data storage 110 and may write ECG data acquired from the patient 170 to the ECG data storage 110. The ECG data storage 110 may comprise non-transitory memory, wherein the ECG data acquired by the data acquisition module 106 may be stored. The ECG data stored in ECG data storage 110 may comprise time series data, wherein an amplitude of the electrical potential difference between two or more of the plurality of electrodes 116 is recorded at regular intervals in time. For example, each recorded electrical potential difference may be time stamped with the time of acquisition, thereby creating time series data. A storage capacity of the ECG data storage 110 may be selected such that an expected number of beats from one or more ECG monitor recordings may be stored thereon. In some embodiments, the ECG data storage 110 may comprise a removable component, enabling a user to physically remove the ECG data storage 110 from the ECG monitor 102. In some embodiments, the ECG data storage 110 may comprise a memory card, a flash drive, or a removable hard drive. In some embodiments, the ECG data storage 110 may be integrated into the ECG monitor 102 and may include a solid state drive (SSD), hard disk drive (HDD).

In an exemplary embodiment, the ECG monitor 102 further comprises an energy storage subsystem 108, wherein electrical energy may be stored, enabling the ECG monitor 102 to operate while attached to a patient for hours or days without the patient to plugging the ECG monitor into an outlet. In some embodiments, the energy storage subsystem 108 comprises a rechargeable battery.

In some embodiments, a communication subsystem 112 may reversibly communicably couple the ECG monitor 102 and the data processing device 120. In one embodiment, the communication subsystem 112 may comprise a wireless or wired connection configured to transfer ECG data from the ECG data storage 110 of the ECG monitor 102 to the data processing device 120. In some embodiments, the communication subsystem 112 may enable the ECG monitor 102 and the data processing device 120 to be in substantially continuous communication via a wireless network, enabling the data processing device 120 to receive substantially real-time ECG data from the ECG monitor 102. As used herein, the term "real-time" refers to a process executed without intentional delay. The communication subsystem 112 may include wired and/or wireless communication devices compatible with one or more different communication protocols. As non-limiting examples, the communication subsystem 112 may be configured to transfer ECG data from the ECG data storage 110 to the data processing device 120 via a wireless network, a wireless local area network, a wired local area network, a wireless wide area network, a wired network, etc. In some embodiments, the communication subsystem 112 may allow the ECG monitor 102 to send and/or receive data to and/or from other devices via a network, such as the public Internet. For example, the communication subsystem 112 may communicatively couple the ECG monitor 102 with the data processing device 120 via a network, such as the public Internet.

The data processing device 120 further receives data from the vital sign monitor 104 via wired or wireless communication. The vital sign monitor 104 includes a plurality of sensors that may each measure one or more vital signs of the patient 170, such as heart rate, blood pressure, oxygen saturation, respiration (e.g., respiration rate), and temperature. For example, the plurality of sensors may include a pulse oximeter, and measurements from the pulse oximeter may be used to determine the oxygen saturation. In some examples, the measurements from the pulse oximeter may be further used to determine the respiration rate and/or the heart rate. As another example, the plurality of sensors 118 may include a blood pressure sensor (e.g., a blood pressure cuff), and data from the blood pressure sensor may be used to determine the blood pressure of the patient 170. In some examples, the heart rate of the patient 170 may be further determined from the blood pressure sensor data. As still another example, the plurality of sensors 118 may include a temperature sensor, and the temperature sensor may measure the temperature of the patient 170.

ECG data acquired by the ECG monitor 102 and vital sign data acquired by the vital sign monitor 104 may be transferred to the data processing device 120 for long term storage, processing (e.g., signal filtering, normalization, noise suppression, etc.), display, and analysis. In one embodiment, the data processing device 120 may comprise a processor 124 configured to execute machine readable instructions stored in a non-transitory memory 126. The processor 124 may be single core or multi-core, and the programs executed thereon may be configured for parallel or distributed processing. In some embodiments, the processor 124 may optionally include individual components that are distributed throughout two or more devices, which may be remotely located and/or configured for coordinated processing. In some embodiments, one or more aspects of the processor 124 may be virtualized and executed by remotely-accessible networked computing devices configured in a cloud computing configuration. In some embodiments, the non-transitory memory 126 may include components disposed at two or more devices, which may be remotely located and/or configured for coordinated processing. In some embodiments, one or more aspects of the non-transitory memory 126 may include remotely-accessible networked storage devices configured in a cloud computing configuration.

The non-transitory memory 126 may store a neural network module 128, which may include a neural network having a tri-net architecture. The neutral network may be trained to predict cardiac arrhythmias by a training module 132, such as according to a training method that will be further described below with respect to FIG. 4. Although the example illustrated in FIG. 1 shows the training module 132 stored on the non-transitory memory 126, in other embodiments, the training module 132 may be stored in a different memory that is not integral to the data processing device 120. The training module 132 may comprise machine executable instructions for training one or more of the neural networks stored in the neural network module 128. In one embodiment, the training module 132 may include gradient descent algorithms, loss functions, and rules for generating and/or selecting training data for use in training a particular neural network.

Further, the neural network module 128 may include instructions for the processor 124 to perform one or more of the steps the method of FIG. 5 to predict the cardiac arrhythmias using the trained neural network, as will be elaborated below. The neural network module 128 may include one or more trained and/or untrained neural networks comprising a plurality of weights and biases, activation functions, loss functions, and instructions for implementing the one or more neural networks to receive ECG data and vital signs data, extract local and contextual features in the ECG data and data from the vital sign monitor 104, and analyze the extracted features, such as will be elaborated below with respect to FIG. 2.

The neural network module 128 may include trained and/or untrained neural networks and may further include various neural network metadata pertaining to the trained and/or untrained networks. In some embodiments, the neural network metadata may include an indication of the training data used to train each neural network, a training method employed to train each neural network, an accuracy/validation score of each neural network, and a type of use-case/protocol for which the trained neural network may be applied.

The non-transitory memory 126 further includes a data storage module 134, which may include ECG monitor data and vital sign data collected from one or more patients. In some embodiments, the data storage module 134 may receive ECG data from ECG monitor 102 and may store the ECG data received therefrom. Similarly, in some embodiments, the data storage module 134 may receive vital sign data from the vital sign monitor 104 and may store the vital sign data received therefrom. In some embodiments, the data processing device 120 may receive ECG data and vital sign data from a plurality of data sources, including one or more network devices. Data stored within the data storage module 134 may be organized according to one or more known organizational schemes or configured into one or more known data structures. In some embodiments, the ECG data and vital sign data may be stored in the data storage module 134 by indexing the data according to patient, acquisition time, originating monitor ID, and so forth.

The data processing device 120 further includes a user input device 140 and a display device 150. The user input device 140 may comprise one or more of a touchscreen, a keyboard, a mouse, a trackpad, a motion sensing camera, or other device configured to enable a user to enter, interact with, and/or manipulate, data within the data processing device 120. The display device 150 may include one or more display devices utilizing any type of display technology, such as a monitor, touchscreen, and/or projector. In some embodiments, the display device 150 may comprise a computer monitor and may display unprocessed and/or processed ECG data and vital signs data. The display device 150 may be combined with the processor 124, the non-transitory memory 126, and/or the user input device 140 in a shared enclosure or may be a peripheral device. A magnified view 151 of the display device 150 is also indicated in FIG. 1, showing representative patient monitoring data including ECG waveforms 152 (e.g., measured by the ECG monitor 102), a heart rate 154, a blood pressure 158, an oxygen saturation 160, a respiration rate 162, and a temperature 164 (e.g., measured by the vital sign monitor 104).

It may be understood that the patient monitoring system 100 shown in FIG. 1 is one exemplary embodiment, and other patient monitoring systems having similar components may also be possible. For example, another appropriate patient monitoring system may include more, fewer, or different components.

Next, FIG. 2 shows a high-level block diagram of an algorithm 200 for cardiac arrhythmia prediction. The algorithm 200 may be run continuously during patient monitoring such that data is analyzed in substantially real-time, as it is acquired. ECG data 202 and patient vitals 204 are input into a local and contextual feature extraction algorithm 206. The ECG data 202 may be acquired via the ECG monitor 102 of FIG. 1, for example, and the patient vitals 204 may be measured by the vital sign monitor 104 of FIG. 1. Further, the ECG data 202 and the patient vitals 204 are measured from a same subject (e.g., the patient 170 of FIG. 1) in order to determine whether or not the subject is expected to develop a cardiac arrhythmia within a number of minutes. The patient vitals 204 may include, for example, a heart rate

208, a blood pressure 210, an oxygen saturation 212, a respiration 214, and a temperature 216.

The local and contextual feature extraction algorithm 206 extracts features at various timescales to model beat-to-beat changes (e.g., local features) as well as longer-term changes (e.g., contextual features), such as heart rate variability. For example, a typical ECG waveform may comprise a P wave during depolarization of the atria, a QRS complex during depolarization of the ventricles, and a T wave during repolarization of the ventricles. This may result in five definable points within the waveform: P, Q, R, S, and T. The local features may include different intervals detected within the ECG data 202 via one or more ECG analytics algorithms, such as a PR interval (e.g., measured from the beginning of the P wave to the beginning of the QRS complex), a RR interval (e.g., measured from a first R wave to a second R wave of a subsequent beat), a QT interval (e.g., measured from the beginning of the QRS complex to the end of the T wave), and so forth. The features extracted by the local and contextual feature extraction algorithm 206 may be used to describe ECG signal morphologies that can be linked to defined physiological events of cardiac activity, such as those described above. The extracted features may further include features that describe the signal and feature extraction quality, such as noise level and/or signal-to-noise ratio.

An exemplary overview of the feature extraction process performed by the local and contextual feature extraction algorithm 206 will now be described. The feature extraction process may begin by filtering the signal from the ECG leads, after which the heartbeats (e.g., the QRS complexes) are detected from the signal. After identifying each heartbeat (also referred to herein as a beat), single beat morphologies/waveforms are identified, and a set of single beat features (e.g., a QRS duration, R amplitude, S amplitude, QT interval, PQ interval) are derived. These single beat features may be derived from a single ECG lead, or they may combine information from multiple ECG leads. The single beat features may also include features that are derived from selectively signal-averaged beats that emphasize the beat type, situation-specific morphologies, and signal-to-noise ratio. These morphologies and/or features of the morphologies may be compared to features on other beat types detected during the measurement. Next, a set of features estimating the feature extraction and signal quality (e.g., the noise level or signal-to-noise ratio) are derived. Finally, a set of features comprising multiple beats are derived from the beat-to-beat/time series of single features that also include a time difference between two beats (e.g., the RR interval). For example, a heart rate that may be derived from the time difference. A further example of these features is a mean RR interval that is defined as the average value of RR intervals over a specified time window (e.g., 5 minutes).

In some embodiments, the local and contextual feature extraction algorithm may be part of the multi-arm neural network 218, while in other embodiments, the local and contextual feature extraction algorithm 206 is distinct from the multi-arm neural network 218. In some embodiments, the local and contextual feature extraction algorithm 206 may perform the extraction of features in training data offline. However, when a patient is being monitored for cardiac arrhythmias, the extraction may be performed online, in real-time. For example, the local and contextual feature extraction algorithm 206 may analyze one heartbeat or signal segment at a time, as the heartbeat or signal segment data is acquired. The extracted features of the heartbeat and/or signal segments may be stored and utilized for widening the feature set to include beat-to-beat (e.g., contextual) features. Thus, the local and contextual feature extraction algorithm 206 may analyze data asynchronously.

The local and contextual feature extraction algorithm 206 outputs extracted features to a multi-arm neural network 218 having a tri-net architecture. The multi-arm neural network 218, also referred to herein as a tri-net neural network (or deep learning model), comprises three subnetworks that model data at different timescales before the modeled data is combined and further modeled (e.g., via a fourth subnetwork). The multi-arm neural network 218 includes transformers for inter-beat temporal dynamics and multilayer perceptron (MLP) combined with a convolutional neural network (CNN) for short-term and long-term modeling, as will be further described below with respect to FIG. 3. The multi-arm neural network 218 outputs an arrhythmia prediction 220, which may include a score for a likelihood of cardiac arrhythmia onset. For example, the score may be a probability value (e.g., ranging from zero to one), as will be further elaborated below with respect to FIG. 5. The score may be compared to a threshold to alert clinicians to a patient developing a cardiac arrhythmia. Additionally or alternatively, the arrhythmia prediction 220 may indicate a presence or absence of an imminent onset of a cardiac arrhythmia. As used herein, "imminent onset" denotes cardiac arrhythmia onset within a number of minutes and less than an hour. The arrhythmia prediction 220 may further include data used in the prediction, which is input into an explainability algorithm 222. The explainability algorithm 222 may identify beats that contribute to the prediction using attention matrices received from the transformers. As an illustrative example, for five beats, the attention matrix will be a 5×5 matrix, with a value in each cell of the matrix indicating a strength of a relationship between one of the beats with another of the beats. The explainability algorithm 222 may further utilize shapely and/or local interpretable model-agnostic explanations (LIME) frameworks to identify long-term features that led to the prediction.

In some embodiments, the explainability algorithm 222 may output a report indicating beat-level features that resulted in a positive arrhythmia prediction. As such, the algorithm 200 not only provides an indication of cardiac arrhythmia prediction, but also identifies and indicates features of the ECG data 202 that contributed to the prediction, enabling clinicians to further evaluate the data to determine if patient intervention is warranted.

Figure 3:
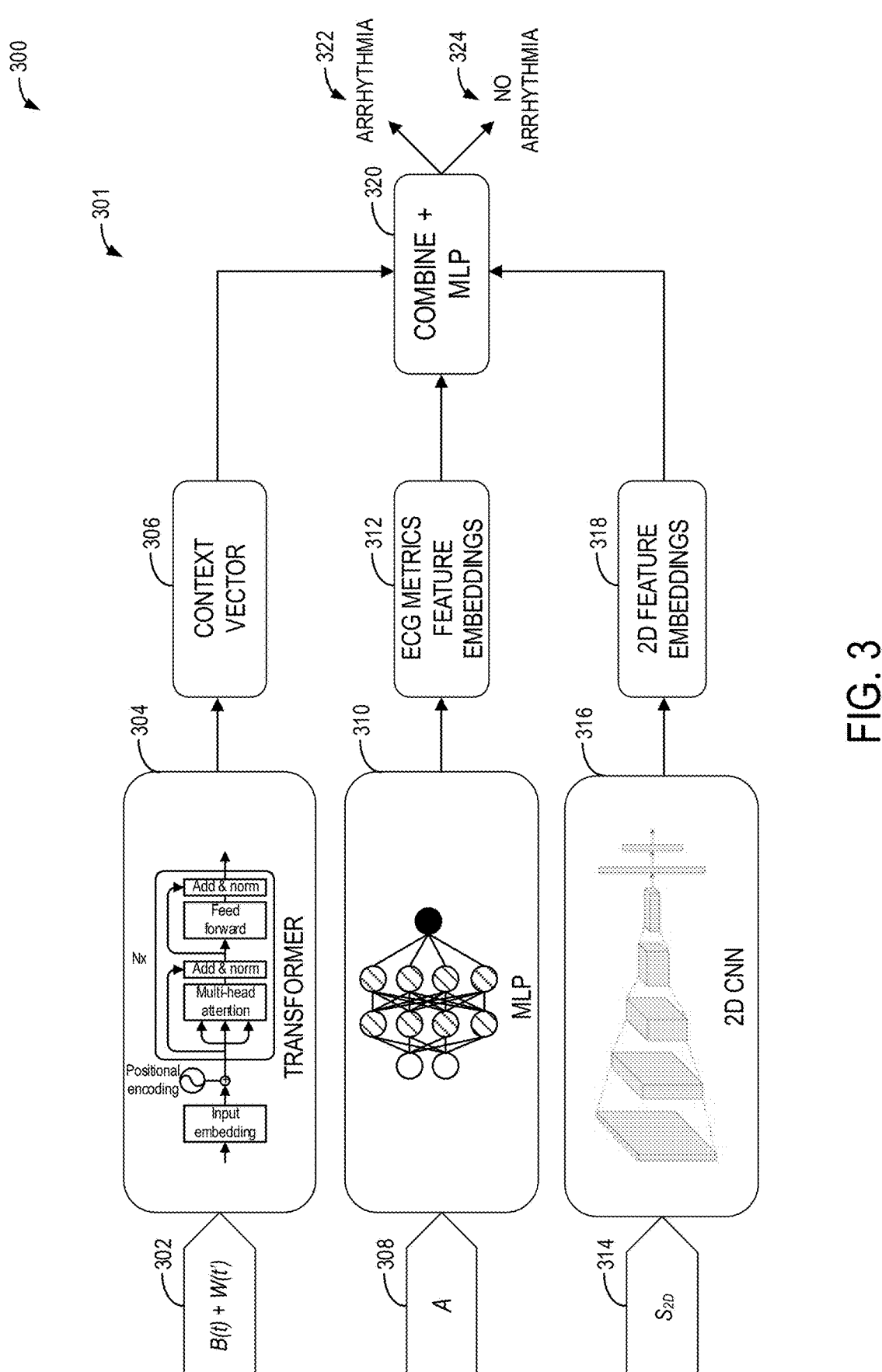
FIG. 3 shows a block diagram of a tri-net neural network architecture for cardiac arrhythmia prediction.

FIG. 3 shows a block diagram of an architecture 300 of a tri-net neural network 301 for cardiac arrhythmia prediction. The tri-net neural network 301 includes three separate neural network arms that are arranged in parallel, including a transformer network 304 (e.g., a first subnetwork), an MLP 310 (e.g., a second subnetwork), and a two-dimensional (2D) CNN 316 (e.g., a third subnetwork). The tri-net neural network 301 represents one embodiment of the multi-arm neural network 218 of FIG. 2. As will be elaborated below, each arm of the tri-net neural network 301 may receive a different subset of the local and contextual features identified by a local and contextual feature extraction algorithm (e.g., the local and contextual feature extraction algorithm 206 of FIG. 2) from multi-modal patient monitoring data comprising ECG data (e.g., ECG data 202 of FIG. 2) and patient vital sign data (e.g., patient vitals 204 of FIG. 2). The outputs of each of the three parallel neural network arms are combined and input into an MLP 320 (e.g., a fourth subnetwork) in series with the three parallel neural network arms, which determines whether or not the input data indicates that a cardiac arrhythmia is expected to occur. Note that while parallel neural network arms are described, in other embodiments, the architecture 300 may additionally or alternatively comprise cascade units that are executed together.

Beat-level features, referred to as B(t), and waveforms, referred to as W(t'), are both temporally varying features that may be determined from ECG data captured from a patient (e.g., the ECG data 202 of FIG. 2). B(t) is a temporally varying feature set for each beat, whereas W(t') is the raw ECG waveform. That is, B(t) comprises features extracted on individual beats from multi-channel data (e.g., the ECG data and other sources of temporally varying data from the patient vital signs data), while W(t') refers to raw multi-lead ECG waveform data. B(t) and W(t') are both examples of local features, where t refers to a beat index and t' refers to sampling time. B(t) and W(t') produce a temporally varying feature set 302, which is input into the transformer network 304.

The transformer network 304 differentially weights a significance of each part of the input temporally varying feature set 302. The transformer network 304 may comprise a plurality of layers, each layer including a self-attention mechanism and a feed-forward neural network. For example, the transformer network 304 may include an encoder-decoder architecture. The transformer network 304 may utilize a scaled dot-product attention architecture, a multi-head attention mechanism, a position-wide feed-forward network, and/or positional encoding. Each encoder may receive encodings from a previous encoder and weigh a relevance of each encoding to each other via one or more self-attention mechanisms to generate output encodings, which are individually processed by the feed forward neural network. The processed output encodings are output to a subsequent encoder as well as the decoders. Further, positional encoding may be used to make use of the order of the data sequence (e.g., with respect to time) of the temporally varying feature set 302. Each decoder may function similarly to the encoders by may include an additional attention mechanism over the encodings in order to identify relevant information between encodings generated by different encoders. The transformer network 304 outputs a context vector 306 based on the input temporally varying feature set 302. The context vector 306 may provide an attention score for each part of the temporally varying feature set 302. For example, the attention score for each part of the temporally varying feature set 302 may be determined from an attention matrix of N×N, where N is a total number of beats analyzed at each prediction. The context vector 306 may be an N×1 vector that is generated by summing up rows of the attention matrix and represents the contribution of each beat to the final arrhythmia prediction. Visualizing the N×1 vector may provide an indication of which beats contribute more to the arrhythmia prediction. Further, by using a threshold on attention scores (e.g., via an explainability algorithm), beats that significantly contributed to an arrhythmia prediction score may be highlighted and output in an explainability report, as will be elaborated herein.

Segment-level and statistical features 308, referred to as A in FIG. 3, include a vector describing a segment of ECG data (e.g., a segment of beats). The vector may include heart rate variability features and statistical metrics for the segments, for example. The segment-level and statistical level features 308 may comprise information about the beat-to-beat variability in the signal, about the trends in the signal, and about the rate of incidents and/or events in the analyzed signal. The trend and event rate features may indicate an overall state and a change in the overall state of the patient, and the beat-to-beat variability features may be linked, for example, to statues of the sympathetic and parasympathetic nervous system of the patient. These segment-level and statistical features 308 differ from the beat-specific features in that they cannot be derived from single beat data, but utilize longer periods of data (e.g., 12 second segments of data).

The segment-level and statistical features 308 are input into the MLP 310. The MLP 310 includes at least three layers of nodes, including an input layer (shown as white filled circles in FIG. 3), one or more hidden layers (shown as diagonally shaded circles in FIG. 3), and an output layer (shown as a black filled circle in FIG. 3). The MLP 310 may classify the segment-level and statistical features 308 and output ECG metrics and feature embeddings 312. For example, the ECG metrics and feature embeddings 312 may include identified ECG features, and the feature embeddings may be used to cluster the ECG metrics in feature space. As such, similar/related ECG metrics may be grouped together at proximal points in the feature space. Thus, the MLP 310 may further simplify the information contained within the segment-level and statistical features 308 into spatially grouped ECG features for further processing by the MLP.

The ECG data comprises frequency content that changes over time and can be represented in both the time domain and the frequency domain. Therefore, the ECG data may be divided into segments obtained over a pre-determined duration, and each segment may be transformed into the frequency domain (e.g., via a Fourier transform) to generate two-dimensional (2D) spectrograms 314, referred to as $S_{2D}$ in FIG. 3. For example, each segment may include continuously acquired ECG data spanning a trailing window of the pre-determined duration. The plurality of segments may be overlapping (e.g., multiple segments contain portions of the same ECG data) or non-overlapping (e.g., each segment includes ECG data that is not included in other segments). In one embodiment, the pre-determined duration is 12 seconds. However, in other embodiments, the duration may be shorter or longer than 12 seconds. When multi-lead ECG data is used, one 2D spectrogram may be generated per channel (e.g., ECG lead), and the spectrograms from each channel may be concatenated before being input into the tri-net neural network 301.

The (concatenated) 2D spectrograms 314 may be input into the 2D CNN 316, which classifies features in the 2D spectrograms 314 and outputs 2D feature embeddings 318. As such, the 2D CNN 316 may summarize the data contained in the 2D spectrograms 314 for further processing by the MLP 320 as well group the 2D features together in feature space based on their similarities relative to each other, such as described above.

The context vector 306, the ECG metrics and feature embeddings 312, and the 2D feature embeddings 318 are all combined and processed via the MLP 320. By first separately processing the temporally varying feature set 302 with the transformer network 304, the segment-level and statistical features 308 via the MLP 310, and the 2D spectrograms 314 via the 2D CNN 316, the MLP 320 may receive a reduced data set that accurately describes the initial data for more efficient and accurate analysis. The MLP 320 outputs an indication of a cardiac arrhythmia 322 (e.g., ventricular fibrillation) or an indication of no cardiac arrhythmia 324. For example, the MLP 320 may generate an arrhythmia prediction score, which may be compared to a pre-determined threshold to determine whether to provide the indication of a cardiac arrhythmia 322 or the indication of no cardiac arrhythmia 324. Thus, the tri-net neural network 301 classifies the input data as being predictive of a cardiac arrhythmia or not predictive of a cardia arrhythmia.

In some embodiments, one or more or each of the transformer network 304, the MLP 310, and the 2D CNN 316 may output an arrhythmia prediction score in addition to extracting features. In such embodiments, the MLP 320 may rectify disagreements in the arrhythmia prediction score (e.g., in the probability that the data is from a pre-arrhythmia heart rhythm) between the different branches as well as providing additional classification of the summarized input data.

Although the above description focuses on features extracted from the ECG data and their analysis, the patient vital sign data may be analyzed similarly. For example, specific feature extraction modules may extract features at different timescales from the patient vital sign data. As an illustrative example, a photoplethysmogram (PPG) waveform obtained from a pulse oximeter may include morphology, amplitude, heart rate variability, other derived features, and raw waveforms. These features may be categorized into the temporally varying feature set 302, the segment-level and statistical features 308, and the 2D spectrograms 314 in an analogous manner to that described above for the ECG data and fed to the corresponding arm of the tri-net neural network 301. For example, 2D spectrograms may be generated from the raw PPG waveforms. As another example, the segment-level and statistical features 308 may comprise features describing the heart rate variability. In still another example, the temporally varying feature set 302 may comprise features describing the morphology and amplitude of the PPG waveform for each beat.

Figure 4:
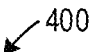
FIG. 4 is a flow chart of a method for training a tri-net deep learning model.
Figure 4:
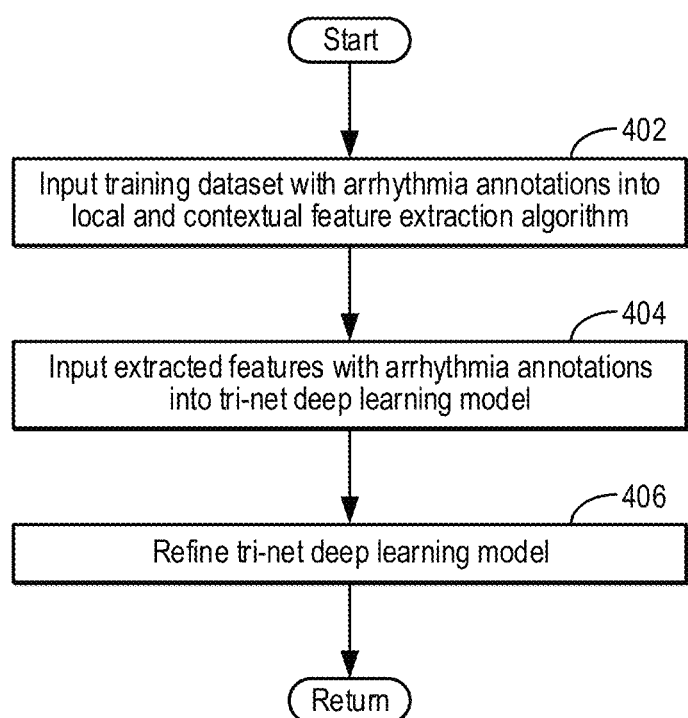

Turning now to FIG. 4, an example method 400 for training a tri-net deep learning model is shown. The method 400 is described with regard to the systems and neural network architectures of FIGS. 1-3, although it may be appreciated that the method 400 may be implemented with other systems and components without departing from the scope of the present disclosure. The method 400 may be carried out according to instructions stored in non-transitory memory of a computing device, such as the data processing device 120 of FIG. 1.

At 402, the method 400 includes inputting a training dataset with arrhythmia annotations into a local and contextual feature extraction algorithm, which may be the local and contextual feature extraction algorithm 206 of FIG. 2 and function as described above. For example, the training dataset may be annotated by clinical experts with ground truth labels and may include data acquired from a plurality of subjects. In some embodiments, an arrhythmia detection algorithm may be used to identify an initial list of potential cardiac arrhythmia cases, and the initial list may be verified by the clinical experts. For each subject, the training dataset may include ECG data and vital sign data obtained over a same time duration with respect to each other. For example, the ECG data (e.g., multi-lead ECG data or single-lead ECG data) may be obtained from a subject over a time period, which may extend a number of minutes, for example, and the vital sign data may be obtained from the same subject over the same time period. As an example, the time period may be in a range from 1 to 10 minutes. Further, a first portion of the plurality of subjects may not experience cardiac arrhythmias and may serve as a control group, while a second, remaining portion of the plurality of subjects may experience a cardiac arrhythmia immediately following the acquired data and may therefore serve as a cardiac arrhythmia group. Thus, the training data for the second portion of the plurality of subjects comprises ECG and vital sign data acquired the number of minutes immediately prior to the onset of a cardiac arrhythmia.

The annotations may indicate that the ECG and vital sign data is negative for cardiac arrhythmia prediction for the control group (e.g., from a patient that has not been diagnosed with a cardiac arrhythmia), while the annotations may indicate that the ECG and vital sign data is positive for cardiac arrhythmia prediction for the cardiac arrhythmia group. In some examples, the data from the cardiac arrhythmia group may be further divided based on the type of cardiac arrhythmia experienced (e.g., ventricular tachycardia, ventricular fibrillation, atrial tachycardia, atrial fibrillation, or another type of arrhythmia). In some embodiments, a single tri-net deep learning model may be trained to predict the onset of multiple types of cardiac arrhythmias that follow similar morphology and cardiac activity. For example, the prediction of different ventricular arrhythmias may be learned by a single model. In other embodiments, separate tri-net deep learning models may be trained for each different type of arrhythmia. For example, a tri-net deep learning model may be trained for predicting ventricular fibrillation, and not other cardiac arrhythmias, using data acquired just prior to the onset of ventricular fibrillation for the cardiac arrhythmia group, and not data for other cardiac arrhythmias (e.g., atrial fibrillation, ventricular tachycardia, and the like). Training separate tri-net deep learning models for distinct types of cardiac arrhythmias may reduce a complexity of the training and increase an accuracy of the model, at least in some examples. Thus, the method 400 may be used to train multiple distinct tri-net deep learning models for predicting the onset of different types of cardiac arrhythmias.

As explained above with respect to FIG. 2, the extracted local and contextual features may include local features that occur on a shorter, beat-to-beat timescale, such as beat-level features and waveforms, and contextual features that occur on a longer timescale that spans a plurality of beats (e.g., segments comprising multiple beats, spectrograms, and statistical features). As such, the extracted features may enable the tri-net neural network to model beat-to-beat changes as well as longer term rate changes. Further, the extracted features may include the arrhythmia annotations so that the subnetworks of the tri-net deep learning model may identify features (e.g., data patterns) that distinguish the data acquired immediately prior to the start of the cardiac arrhythmia from the normal heart rhythm data.

Although the above description discusses a training dataset comprising both ECG data and patient vital sign data, in other embodiments, the training dataset may comprise only ECG data. For example, the training dataset may comprise both ECG data and patient vital sign data when the resulting trained tri-net deep learning network is configured to predict cardiac arrhythmias using both ECG data and patient vital sign data as the input, or the training dataset may comprise only ECG data when the resulting trained tri-net deep learning network is configured to predict cardiac arrhythmias based on only ECG data as the input. As an illustrative embodiment, single-lead ECG data may be used to train the tri-net deep learning model, which may simplify the training process by reducing a number of inputs and layers used in the model.

At 404, the method 400 includes inputting the extracted features with arrhythmia annotations into the tri-net deep learning model. The tri-net deep learning model may receive features that occur on a shorter, beat-to-beat timescale (e.g., such as beat-level features and waveforms), segment-level features that occur over a longer timescale including a plurality of beats, and spectrograms extracted from ECG segments acquired over the longer timescale, which may be each input into the appropriate arm of the tri-net deep learning model. For example, a transformer network may receive the beat-level features, a first MLP may receive segment-level features, and a 2D CNN may receive the spectrograms, such as described above with respect to FIG. 3. Further, tri-net deep learning network may be initialized with random weights and biases at the beginning of the training. The resulting outputs from each arm of the tri-net deep learning model may be combined and input into a second MLP, which may output an arrhythmia prediction.

At 406, the method 400 includes refining the tri-net deep learning model. A loss may be determined based on the arrhythmia prediction (e.g., arrhythmia predicted or no arrhythmia predicted) compared with the ground truth labels, and the weights and biases may be adjusted using an optimization algorithm (e.g., a gradient descent algorithm). Further, the loss may be backpropagated through the second MLP and all three branches feeding the second MLP simultaneously so that the parameters of each subnetwork may be simultaneously updated based on a same loss.

The method 400 may then return. For example, method 400 may be repeated until one or more pre-determined conditions are met. In some embodiments, the one or more pre-determined conditions may include convergence of the weights and biases of the tri-net deep learning model (that is, a rate of change of the parameters of each subnetwork of the tri-net deep learning model decreases to below a pre-determined threshold rate), the loss determined at 406 decreasing to below a pre-determined, non-zero, threshold, etc. In some embodiments, the loss may be determined using a validation dataset, wherein the validation dataset is distinct from the training dataset and comprises data not seen by the tri-net deep learning model during training. In this way, the method 400 enables the tri-net deep neural network to learn features of ECG data and vital sign data that enable cardiac arrhythmias to be predicted before they occur.

Figure 5:
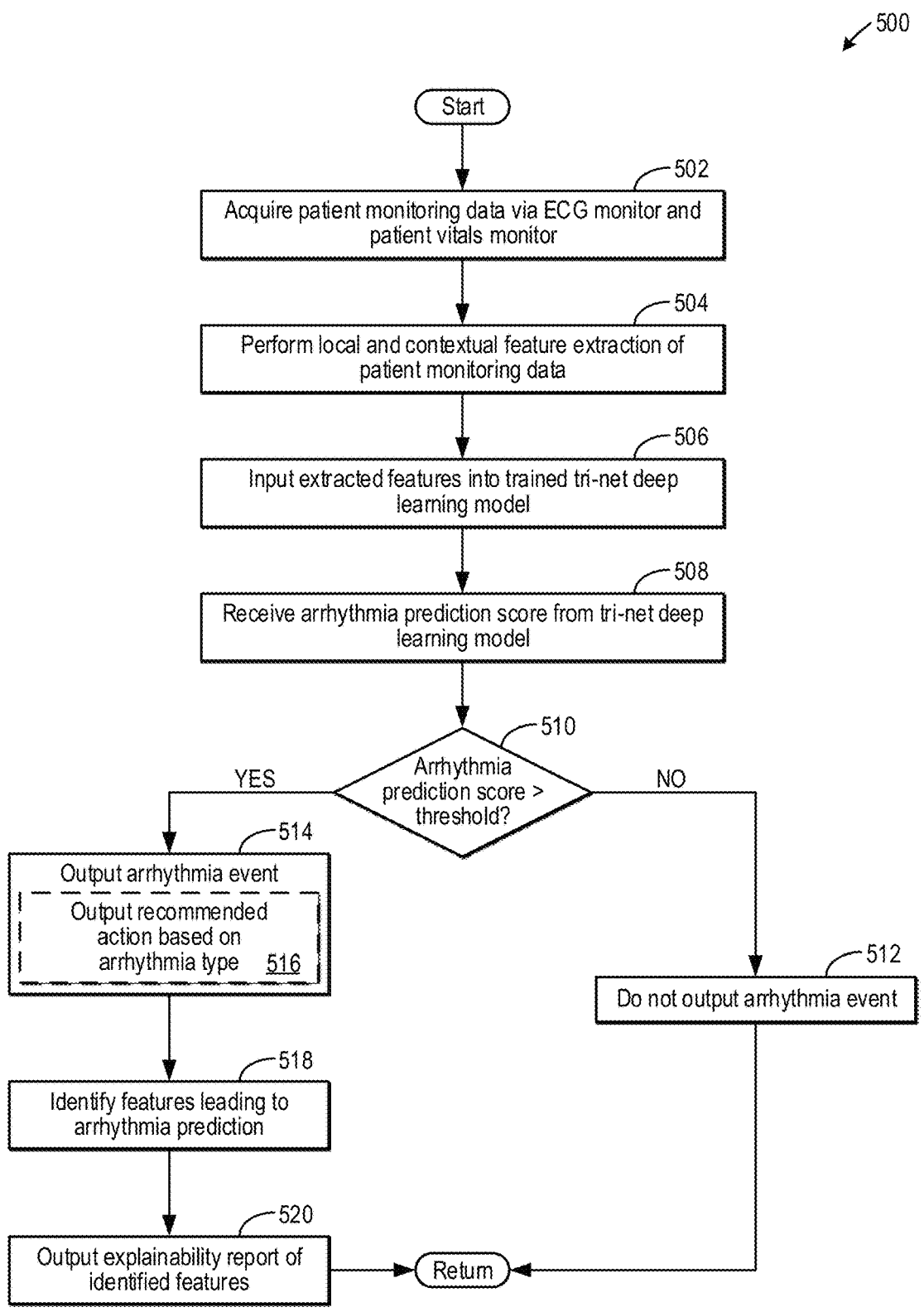
FIG. 5 is a flow chart of a method for using a tri-net deep learning model to predict cardiac arrhythmias before onset.

FIG. 5 shows an example method 500 for predicting cardiac arrhythmias via a tri-net deep learning model. The method 500 is described with regard to the systems and neural network architectures of FIGS. 1-3, although it may be appreciated that the method 500 may be implemented with other systems and components without departing from the scope of the present disclosure. The method 500 may be carried out according to instructions stored in non-transitory memory of a computing device, such as the data processing device 120 of FIG. 1.

At 502, the method 500 includes acquiring patient monitoring data via an ECG monitor and a patient vital sign monitor. For example, the patient monitoring data may include single-lead ECG data or multi-lead ECG data acquired from a patient (e.g., acquired by the ECG monitor 102 of FIG. 1) as well as one or more of a heart rate, blood pressure, oxygen saturation, respiration, and temperature of the patient (e.g., acquired by the vital sign monitor 104 of FIG. 1). However, it may be appreciated that in alternative embodiments, the patient monitoring data may comprise only the ECG data.

At 504, the method 500 includes performing local and contextual feature extraction of the patient monitoring data. As described above with respect to FIG. 2, the patient monitoring data may be processed by a local and contextual feature extraction algorithm that identifies local features that occur on a beat-to-beat time scale and contextual features that occur over multiple beats. As one example, the patient monitoring data may be processed as segments of a pre-determined duration (e.g., 12 seconds) are acquired. Further, new patient monitoring data may continue to be acquired as previously acquired patient monitoring data is processed by the local and contextual feature extraction algorithm.

At 506, the method 500 includes inputting the extracted features into a trained tri-net deep learning model. The tri-net deep learning model may have the architecture described with respect to FIG. 3 and may be trained according to the method of FIG. 4. As stated above, three different subnetworks of the tri-net deep learning model may process different features extracted by the local and contextual feature extraction algorithm. For example, a transformer network may process local features to identify and differentially weight inter-beat temporal dynamics (e.g., via an attention score), a first MLP may process segment-level and statistical features to identify and cluster ECG metrics, and a 2D CNN may process 2D spectrograms generated from the ECG data to identify and cluster features of the 2D spectrograms. The tri-net deep learning model may be trained to predict the onset of one or more cardiac arrhythmias. Thus, in some embodiments, the extracted features may be input into a plurality of tri-net deep learning models, each of the plurality of tri-net deep learning models trained to predict the onset of one type of cardiac arrhythmia (e.g., ventricular fibrillation only) or a class of arrhythmias having similar cardiac features (e.g., ventricular arrhythmias only). In other embodiments, the tri-net deep learning model may be broadly trained to more generically predict cardiac arrhythmias.

At 508, the method 500 includes receiving an arrhythmia prediction score from the tri-net deep learning model. The resulting vectors and feature embeddings output by the three different subnetworks of the tri-net deep learning model may be input into a second MLP, which may output the arrhythmia prediction score. The arrhythmia prediction score may range from zero to one, for example, where zero represents a lowest probability of the patient experiencing imminent cardiac arrhythmia (e.g., within a number of minutes) and one represents a highest probability of the patient experiencing imminent cardiac arrhythmia. Thus, the arrhythmia prediction score may also be referred to as an arrhythmia probability score.

At 510, the method 500 includes determining if the arrhythmia prediction score is greater than a threshold. The threshold may be a pre-determined value between zero and one, such as a value between 0.6 and 0.9 (e.g., 0.7). If the arrhythmia prediction score is not greater than the threshold (e.g., the arrhythmia prediction score is less than or equal to the threshold), the method 500 proceeds to 512 and includes not outputting an arrhythmia event, which will be further described below at 514. The method 500 may then return. For example, the patient monitoring data may continue to be analyzed so that an imminent onset of cardiac arrhythmia may be predicted should the patient's status change.

If the arrhythmia prediction score is greater than the threshold, the method 500 proceeds to 514 and includes outputting the arrhythmia event. For example, the arrhythmia event may include a visual message or graphic that is output to one or more devices, such as a display device displaying the patient monitoring data (e.g., the display device 150 of FIG. 1) and/or an electronic device of a treating clinician (e.g., a smartphone). Further, the arrhythmia event may include an audible message or tone in addition to or as an alternative to the visual message. In some embodiments, the arrhythmia event may include an indication that a cardiac arrhythmia has been predicted as well as the type of arrhythmia predicted. Additionally or alternatively, the arrhythmia event may include a risk score for the patient developing the cardiac arrhythmia. For example, the risk score may increase as the arrhythmia prediction score further increases above the threshold. In some embodiments, the arrhythmia event may be saved to the patient's electronic medical record so that the prediction may be documented. Further, in some embodiments, outputting the arrhythmia event may further include outputting a recommended action based on the arrhythmia type, as optionally indicated at 516. For example, if the type of arrhythmia detected is shockable, the recommended action may include outputting instructions to prepare a defibrillator. As another example, the recommended action may include preparing for cardiopulmonary resuscitation or another form of treatment.

At 518, the method 500 includes identifying features leading to the arrhythmia prediction. For example, an explainability algorithm (e.g., the explainability algorithm 222 of FIG. 2) may use attention matrices to identify beats that contribute to the arrhythmia prediction, such as according to self-attention profiles from the transformer network, and may further utilize shapely and/or local interpretable model-agnostic explanations frameworks to identify longer-term features (e.g., heart rate variability) that led to the arrhythmia prediction. In particular, the explainability algorithm may assess the data acquired after the arrhythmia prediction score first exceeded the threshold.

At 520, the method 500 includes outputting an explainability report of the identified features. The explainability report may include graphics and/or text-based descriptions of the identified features. For example, the explainability report may include an illustration of ECG data with annotations highlighting particular beats that contributed to the higher than threshold arrhythmia prediction score. As another example, a graph of the self-attention profiles may be included in the explainability report in response to a user request. The explainability report may be output to the display device, for example. In some embodiments, the explainability report may be additionally saved to the patient's electronic medical record. The method 500 may then return.

Next, FIG. 6 shows a set of graphs 600 illustrating ventricular fibrillation prediction using the algorithm 200 described with respect to FIG. 2, the tri-net deep learning model having the architecture 300 described with respect to FIG. 3, and the method 500 described with respect to FIG. 5. A horizontal axis represents time, while a vertical axis represents an arrhythmia prediction score in each graph in the set of graphs 600. The set of graphs 600 includes a first graph 602 comprising data from a first patient, a second graph 604 comprising data from a second patient, a third graph 606 comprising data from a third patient, a fourth graph 608 comprising data from a fourth patient, a fifth graph 610 comprising data from a fifth patient, and a sixth graph 612 comprising data from a sixth patient. Further, a threshold score 614 is illustrated in each graph in the set of graphs 600, indicated by a horizontal dashed line. The threshold score 614 defines an arrhythmia prediction score above which cardiac arrhythmia onset is predicted. Further still, each graph in the set of graphs 600 includes a VF plot 616, which represents a cardiac arrhythmia score for VF. The VF plot 616 of each individual graph is generated using the tri-net deep learning model based on ECG data and patient vitals for a single patient during a defined time period. Although FIG. 6 will be described for predicting VF, it may be understood that plots for any other type of cardia arrhythmia may be similarly generated and analyzed.

For the first graph 602, the VF plot 616 crosses the threshold score 614 at a time t1, and thus, VF is predicted at time t1. For example, an arrhythmia event 618, represented by a small-dashed vertical line, may be output at time t1 in response to VF being predicted at time t1. For example, the arrhythmia event 618 may include a visual and/or audible alarm or other message that is output to clinicians. A VF onset indicator 620, represented by a dashed vertical line, is output at a time t2, which is approximately 4 minutes after the VF was predicted. The VF onset indicator 620 indicates when ventricular fibrillation is first detected in the first patient. Thus, clinicians treating the first patient may be alerted 4 minutes in advance, enabling them to prepare for the VF onset.

For the second graph 604, the VF plot 616 crosses the threshold score 614 at a time t3, and thus, the arrhythmia event 618 is output at time t3. For example, the event may be output at time t3 in response to VF being predicted at time t3. VF onset begins at a time t4, as indicated by the VF onset indicator 620 at time t4, which is approximately 7 minutes after the VF was predicted. Thus, clinicians treating the second patient may be alerted 7 minutes in advance, enabling them to prepare for the VF onset.

For the third graph 606, the VF plot 616 crosses the threshold score 614 at a time t5, and thus, VF is predicted at the time t5. In response to VF being predicted at time t5, the arrhythmia event 618 is output at time t5. VF onset begins at a time t6, as indicated by the VF onset indicator 620, which is approximately 19 minutes after the VF was predicted (e.g., the arrhythmia event 618 output at time t5). Thus, clinicians treating the third patient may be alerted 19 minutes in advance, enabling them to prepare for the VF onset.

In contrast, the VF plot 616 does not cross the threshold score 614 for any of the fourth graph 608, the fifth graph 610, or the sixth graph 612. As such, VF is not predicted for the fourth patient, the fifth patient, or the sixth patient. Further, none of the fourth patient, the fifth patient, and the sixth patient go into VF, indicating that the algorithm 200 may accurate predict the presence or absence of impending cardiac arrhythmias.

FIG. 7 shows a set of graphs 700 illustrating cardiac arrhythmia prediction explainability, using the third graph 606 introduced in FIG. 6 as an example. Thus, the third graph 606 is replicated in FIG. 7, including the VF plot 616, the threshold score 614, the arrhythmia event 618 at time t5, and the VF onset indicator 620 at time t6. A self-attention plot 702 and an ECG plot 704 each include data acquired during the pre-VF region between time t5 and time t6 of the third graph 606, shown as a duration 701. The self-attention plot 702 shows a visualization of an attention matrix plotted as vectors for all of the beats in the ECG plot 704. Because there are 30 beats in the present example, the self-attention plot 702 includes 30 overlapping plots. The attention matrix may be received from transformers of a transformer network of a tri-net deep learning model, such as the transformer network 304 of FIG. 3, and the ECG plot 704 shows ECG beat-to-beat data that is analyzed by the transformer network. For the self-attention plot 702, the horizontal axis represents ECG beat number, while the vertical axis represents a self-attention score. As the self-attention score increases, a relevance of the corresponding ECG beat to the cardiac arrhythmia prediction increases. For the ECG plot 704, the horizontal axis represents time (e.g., in seconds), while the vertical axis represents voltage.

An explainability algorithm (e.g., the explainability algorithm 222) may identify which beats contributed the most to the VF prediction, as highlighted by indicators 706 on the ECG plot 704. The explainability algorithm may determine a threshold value for identifying beats that contribute more to the VF prediction as a function of the number of beats analyzed. For example, the threshold value may be the average attention score. Because the attention scores add up to 1, the threshold value may be calculated as 1/N, where N is the number of beats analyzed. For example, if all of the N beats contributed equally, each beat would have an attention score of 1/N. Therefore, beats that contribute more than the average (e.g., more than 1/N) are considered to be more relevant to the arrhythmia prediction. Thus, in the example shown in FIG. 7, the threshold value is 0.033, and beats in the ECG plot 704 that each have an attention score greater than 0.033 are annotated with the indicators 706 to distinguish those particular beats. The indicators 706 are shown in FIG. 7 as boxes surrounding the beats having the greater than threshold value attention score. However, the indicators 706 may use other types of annotations, such as lines, arrows, other shapes, and/or colors, to distinguish the beats contributing the most to the VF prediction from other beats in the ECG plot 704. As such, the explainability report may visually distinguish the beats that are the largest contributors to the VF prediction so that these beats may be reviewed by a clinician.

In this way, a tri-net neural network that models multi-modal patient data on different timescales may be used to predict cardiac arrhythmias before they occur, enabling proactive intervention. Further, an explainability report highlighting beat-level features contributing to the prediction may be output to a clinician, thereby allowing the clinician to evaluate the beat-level features to determine whether intervention is likely warranted or not. Overall, positive patient outcomes may be increased. A technical effect of modeling both shorter term dynamics and longer term dynamics in multi-modal patient data that includes ECG data is that cardiac arrhythmias may be accurately predicted by a multi-arm deep learning network before their onset.

The disclosure also provides support for a method, comprising: predicting an imminent onset of a cardiac arrhythmia in a patient, before the cardiac arrhythmia occurs, by analyzing patient monitoring data via a multi-arm deep learning model, outputting an arrhythmia event in response to the prediction, and outputting a report indicating features of the patient monitoring data contributing to the prediction. In a first example of the method, the patient monitoring data comprises electrocardiogram (ECG) data acquired from the patient, and the report indicates beats of the ECG data contributing to the prediction. In a second example of the method, optionally including the first example, the report is generated via an explainability algorithm that receives attention matrices of the beats of the ECG data generated by a transformer network of the multi-arm deep learning model. In a third example of the method, optionally including one or both of the first and second examples, local features and contextual features of the multi-modal patient monitoring data are extracted by a feature extraction algorithm prior to being input into the multi-arm deep learning model. In a fourth example of the method, optionally including one or more or each of the first through third examples, the multi-arm deep learning model comprises three parallel neural network arms, and wherein each of the three parallel neural network arms receives a different subset of the extracted local features and contextual features. In a fifth example of the method, optionally including one or more or each of the first through fourth examples, the multi-arm deep learning model comprises a transformer network, a first multilayer perceptron, and a two-dimensional convolutional neural network. In a sixth example of the method, optionally including one or more or each of the first through fifth examples, the extracted local features comprise beat-level features of the patient monitoring data and waveforms of the patient monitoring data, and wherein the extracted contextual features comprise multi-beat segment-level features and two-dimensional spectrograms comprising a frequency domain transform of a multi-beat segment of the patient monitoring data. In a seventh example of the method, optionally including one or more or each of the first through sixth examples, analyzing the patient monitoring data via the multi-arm deep learning model comprises: combining the beat-level features of the patient monitoring data and the waveforms of the patient monitoring data to produce a temporally varying feature set, inputting the temporally varying feature set into the transformer network, inputting the multi-beat segment-level features into the first multilayer perceptron, and inputting the two-dimensional spectrograms into the two-dimensional convolutional neural network. In an eighth example of the method, optionally including one or more or each of the first through seventh examples, analyzing the patient monitoring data via the multi-arm deep learning model further comprises: inputting an output of each of the transformer network, the first multilayer perceptron, and the two-dimensional convolutional neural network into a second multilayer perceptron, and receiving an arrhythmia prediction score from the second multilayer perceptron. In a ninth example of the method, optionally including one or more or each of the first through eighth examples, predicting the imminent onset of the cardiac arrhythmia in the patient is in response to the arrhythmia prediction score being greater than a threshold score, and wherein the cardiac arrhythmia is one of ventricular fibrillation, atrial fibrillation, and ventricular tachycardia.

The disclosure also provides support for a method, comprising: acquiring electrocardiogram (ECG) data from a patient, extracting local and contextual features from the ECG data as the ECG data is acquired, inputting the extracted local and contextual features into a multi-arm neural network, predicting whether or not an imminent ventricular fibrillation is expected to occur in the patient based on an output of the multi-arm neural network, and outputting an arrhythmia event and an explainability report indicating portions of the ECG data contributing to the prediction in response to the imminent ventricular fibrillation being expected to occur in the patient. In a first example of the method, the ECG data is single-lead ECG data. In a second example of the method, optionally including the first example, the multi-arm neural network comprises a first subnetwork, a second subnetwork, a third subnetwork, and a fourth subnetwork that receives an input that combines outputs of each of the first subnetwork, the second subnetwork, and the third subnetwork. In a third example of the method, optionally including one or both of the first and second examples, the first subnetwork comprises a transformer network, the second subnetwork comprises a first multilayer perceptron, the third subnetwork comprises a convolutional neural network, and the fourth subnetwork comprises a second multilayer perceptron. In a fourth example of the method, optionally including one or more or each of the first through third examples, the second multilayer perceptron outputs a ventricular fibrillation probability score, and wherein predicting whether or not the imminent ventricular fibrillation is expected to occur in the patient based on the output of the multi-arm neural network comprises: predicting the imminent ventricular fibrillation is expected to occur in the patient in response to the ventricular fibrillation probability score being greater than a threshold score, and predicting the imminent ventricular fibrillation is not expected to occur in the patient in response to the ventricular fibrillation probability score being less than or equal to the threshold score.

The disclosure also provides support for a system, comprising: a display device, and a computing device operably coupled to the display device and storing instructions executable to: receive patient monitoring data acquired from a patient, predict whether an imminent cardiac arrhythmia is expected to occur in the patient by analyzing the patient monitoring data via a multi-arm deep learning model, output an arrhythmia event to the display device in response to the imminent cardiac arrhythmia being expected to occur, identify portions of the patient monitoring data leading to the prediction in response to the imminent cardiac arrhythmia being expected to occur, and output an explainability report of the identified portions to the display device. In a first example of the system, the patient monitoring data comprises one or more of electrocardiogram (ECG) data and patient vital sign data, and wherein local and contextual features of the ECG data and the patient vital sign data are extracted by an algorithm in real-time as the multi-modal patient monitoring data is acquired, and the extracted local and contextual features are input into the multi-arm deep learning model. In a second example of the system, optionally including the first example, the multi-arm deep learning model comprises three parallel subnetworks that each receive different subsets of the extracted local and contextual features and a fourth subnetwork in series with the three parallel subnetworks. In a third example of the system, optionally including one or both of the first and second examples, the three parallel subnetworks comprise a transformer network that models the extracted local features, a first multilayer perceptron that models the contextual features, and a convolutional neural network that models two-dimensional spectrograms extracted from the ECG data. In a fourth example of the system, optionally including one or more or each of the first through third examples, the identified portions include beats of the ECG data having higher than a threshold attention scores output by the transformer network.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
predicting an imminent onset of a cardiac arrhythmia in a patient, before the cardiac arrhythmia occurs, by analyzing patient monitoring data via a multi-arm deep learning model comprising a transformer network having an encoder portion and a decoder portion, a first multilayer perceptron, and a two-dimensional convolutional neural network (CNN), wherein analyzing the patient monitoring data via the multi-arm deep learning model comprises:
extracting local features of the patient monitoring data, the local features including beat-level features of the patient monitoring data and waveforms of the patient monitoring data;
extracting contextual features of the patient monitoring data, the contextual features including multi-beat segment-level features of the patient monitoring data;
generating two-dimensional (2D) spectrograms comprising a frequency domain transform of multi-beat segments of the patient monitoring data;
combining the beat-level features of the patient monitoring data and the waveforms of the patient monitoring data to produce a temporally varying feature set;
inputting the temporally varying feature set into the transformer network, wherein the temporally varying feature set is encoded by the encoder portion, and then decoded by the decoder portion of the transformer network;
inputting the multi-beat segment-level features into the first multilayer perceptron; inputting the two-dimensional spectrograms into the 2D CNN;
inputting an output of each of the transformer network, the first multilayer perceptron, and the 2D CNN into a second multilayer perceptron; and receiving an arrhythmia prediction score from the second multilayer perceptron, wherein predicting the imminent onset of the cardiac arrhythmia in the patient is in response to the arrhythmia prediction score being greater than a threshold score;
outputting an arrhythmia event in response to the prediction; and outputting a report indicating features of the patient monitoring data contributing to the prediction.

2. The method of claim 1, wherein the patient monitoring data comprises electrocardiogram (ECG) data acquired from the patient, and the report indicates beats of the ECG data contributing to the prediction.

3. The method of claim 2, wherein the report is generated via an explainability algorithm that receives attention matrices of the beats of the ECG data generated by the transformer network of the multi-arm deep learning model.

4. The method of claim 2, wherein the extracted local features comprise:
a PR interval measured from a beginning of a P wave of the ECG data to a beginning of a ORS complex of the ECG data;
an RR interval measured from a first R wave to a second R wave of a subsequent beat of the ECG data; and
a QT interval measured from the beginning of the ORS complex to an end of a T wave of the ECG data.

5. The method of claim 2, wherein the extracted local and/or contextual features further include a noise level and a signal-to-noise ratio.

6. The method of claim 1, wherein the local features and the contextual features are extracted by a feature extraction algorithm prior to being input into the multi-arm deep learning model.

7. The method of claim 1, wherein the extracted local and/or contextual features further include arrhythmia annotations.

8. The method of claim 1, wherein the cardiac arrhythmia is one of ventricular fibrillation, atrial fibrillation, and ventricular tachycardia.

9. A method, comprising:

acquiring electrocardiogram (ECG) data from a patient;

extracting local and contextual features from the ECG data as the ECG data is acquired, the local features including beat-level features of the ECG data and waveforms of the ECG data, the contextual features including features of multi-beat segments of the ECG data;

inputting the beat-level features of the ECG data and the waveforms of the ECG data into a transformer network, wherein the beat-level features of the ECG data and the waveforms of the ECG data are encoded by an encoder portion, and then decoded by a decoder portion of the transformer network;

inputting the multi-beat segment features into a first multilayer perceptron;

inputting two-dimensional (2D) spectrograms comprising a frequency domain transform of the multi-beat segments into a 2D convolutional neural network (CNN);

inputting an output of each of the transformer network, the first multilayer perceptron, and the 2D CNN into a second multilayer perceptron;

predicting whether or not an imminent ventricular fibrillation is expected to occur in the patient based on an output of the second multilayer perceptron, wherein the second multilayer perceptron outputs a ventricular fibrillation probability score and wherein predicting whether or not the imminent ventricular fibrillation is expected to occur in the patient based on the output of the second multilayer perceptron comprises:

predicting the imminent ventricular fibrillation is expected to occur in the patient in response to the ventricular fibrillation probability score being greater than a threshold score; and predicting the imminent ventricular fibrillation is not expected to occur in the patient in response to the ventricular fibrillation probability score being less than or equal to the threshold score; and outputting an arrhythmia event and an explainability report indicating portions of the ECG data contributing to the prediction in response to the imminent ventricular fibrillation being expected to occur in the patient.

10. The method of claim 9, wherein the ECG data is single-lead ECG data.

11. The method of claim 9, wherein the explainability report is generated using an explainability algorithm that identifies beats of the ECG data contributing to the predication using an attention matrix received from transformer network.

12. A system, comprising:

a display device; and a computing device operably coupled to the display device and storing instructions executable to:

receive patient monitoring data acquired from a patient, wherein the patient monitoring data comprises at least electrocardiogram (ECG) data;

predict whether an imminent cardiac arrhythmia is expected to occur in the patient by analyzing the patient monitoring data via a multi-arm deep learning model;

output an arrhythmia event to the display device in response to the imminent cardiac arrhythmia being expected to occur;

identify portions of the patient monitoring data leading to the prediction in response to the imminent cardiac arrhythmia being expected to occur, wherein the identified portions include beats of the ECG data having higher than a threshold attention scores output by a transformer network of the multi-arm deep learning model, wherein the identified portions of the patient monitoring data are encoded by an encoder portion, and then decoded by a decoder portion of the transformer network; and output an explainability report of the identified portions to the display device;

wherein further instructions are stored in the computing device executable to:

extract local and contextual features from the ECG data as the ECG data is acquired, the local features including beat-level features of the ECG data and waveforms of the ECG data, the contextual features including features of multi-beat segments of the ECG data;

input the beat-level features of the ECG data and the waveforms of the ECG data into the transformer network;

input the multi-beat segment features into a first multilayer perceptron;

input two-dimensional (2D) spectrograms comprising a frequency domain transform of the multi-beat segments into a 2D convolutional neural network (CNN);

input an output of each of the transformer network, the first multilayer perceptron, and the 2D CNN into a second multilayer perceptron; and receive a prediction of the imminent cardiac arrhythmia as an output of the second multilayer perceptron.

13. The system of claim 12, wherein the patient monitoring data further comprises patient vital sign data, and wherein local and contextual features of the ECG data and the patient vital sign data are extracted by an algorithm in real-time as the patient monitoring data is acquired, and the extracted local and contextual features are input into the multi-arm deep learning model.

14. The system of claim 13, wherein the multi-arm deep learning model comprises three parallel subnetworks that each receive different subsets of the extracted local and contextual features and a fourth subnetwork in series with the three parallel subnetworks.

* * * * *